US008751209B2

United States Patent
Henning et al.

(10) Patent No.: US 8,751,209 B2
(45) Date of Patent: Jun. 10, 2014

(54) SIMULATION CACHE TO EXPEDITE COMPLEX MODELING AND SIMULATION PROCESSES

(75) Inventors: Mark Daniel Henning, Maple Grove, MN (US); Michael J. Smith, Forest Hill, MD (US); Javad Sedehi, Alexandria, VA (US); William Crocoll, Broadlands, VA (US)

(73) Assignee: Exelis Inc., McLean, VA (US)

( * ) Notice: Subject to any disclaimer, the term of this patent is extended or adjusted under 35 U.S.C. 154(b) by 1016 days.

(21) Appl. No.: 11/686,170

(22) Filed: Mar. 14, 2007

(65) Prior Publication Data

US 2010/0268519 A1 Oct. 21, 2010

(51) Int. Cl.
*G06F 7/60* (2006.01)
*G06F 17/10* (2006.01)
*G06G 7/48* (2006.01)
*G06G 7/56* (2006.01)
*G06G 7/62* (2006.01)
*G01N 33/48* (2006.01)
*G01N 33/50* (2006.01)
*G01N 31/00* (2006.01)
*G01N 7/00* (2006.01)
*G01N 19/10* (2006.01)
*G01C 17/38* (2006.01)

(52) U.S. Cl.
USPC .......................................................... 703/13

(58) Field of Classification Search
USPC ........... 703/13, 2, 5; 702/19, 22, 95; 73/31.02
See application file for complete search history.

(56) References Cited

U.S. PATENT DOCUMENTS

| | | | |
|---|---|---|---|
| 6,996,478 B2 * | 2/2006 | Sunshine et al. | 702/22 |
| 7,102,514 B2 | 9/2006 | Berry | |
| 7,542,884 B2 * | 6/2009 | Boris et al. | 703/2 |
| 2007/0038383 A1 * | 2/2007 | Boris et al. | 702/19 |
| 2007/0288208 A1 * | 12/2007 | Grigsby et al. | 703/2 |

OTHER PUBLICATIONS

Michael J. Smith, Javad Sedehi, Stuart Edick, Mark Henning, and William Crocoll, Sensor Location and Optimization Tool Set (SLOTS), ITT Industries Advanced Engineering and Science, 2005.*

(Continued)

*Primary Examiner* — Saif Alhija
*Assistant Examiner* — Angel Calle
(74) *Attorney, Agent, or Firm* — Edell, Shapiro & Finnan, LLC

(57) ABSTRACT

A method is provided for determining optimum positions in a region for a plurality of sensors that are capable of detecting occurrence of a hazard in the region. The hazard may be a chemical, biological, and/or radiological hazard in solid, liquid or gas form. A "simulation cache" is provided that stores data representing interaction of the hazard with sensors at each of the plurality of candidate locations in the region for each of the plurality of sensor types. Data is then retrieved from the simulation cache as needed for evaluation a particular candidate sensor solution comprising one or more sensors of one or more sensor types at corresponding ones of the candidate locations. An optimization algorithm may be used to select a candidate sensor solution. The data that is retrieved from the simulation cache for a selected candidate sensor solution is evaluated with respect to certain performance criteria. The simulation cache greatly reduces the time required to generate an optimum sensor layout because it separates the hazard modeling and sensor performance modeling from the optimization algorithm. By capturing this data at one time for storage in the simulation cache, it is not necessary to re-run the hazard simulations for each candidate sensor location generated by the optimization algorithm.

20 Claims, 5 Drawing Sheets

(56) References Cited

OTHER PUBLICATIONS

Ronald W. Lee and James J. Kulesz, "A risk based sensor placement methodology", ORNL/TM, May 15, 2006.*
Michael J. Smith, "Sensor location and optimization tool set (SLOTS)", 2005.*
Abhishek Chugh, NPL, "Towards adaptive caching for parallel and discrete event simulation", 2004.*
Jay Boris, NPL, "Using CT-ANALYST™ to optimize sensor placement", 2004.*
Theodore Young, Jr., NPL, "Emergency assessment with sensors and buildings: Advances in CT-ANALYST technology", 2004.*
Michael J. Smith, Javad Sedehi, Stuart Edick, Mark Henning, William Crocoll, "Sensor Location and Optimization Tool Set (Slots)," Presentation at the National Defense Initiative Association on Oct. 27, 2005, Science and Technology for Chem-Bio Information Systems (S&T CBIS).
Sharon Padula, Rex K. Kincaid, "Optimization Strategies for Sensor and Actuator Placement," NASA/TM-1999-20926, Apr. 1999, Langley Research Center, Hampton, VA.
Santpal S. Dhillon, Krishnendu Chakrabarty, S.S. Iyengar, "Sensor Placement for Grid Coverage Under Imprecise Detections," in Proceedings of the International Conference on Information Fusion (FUSION 2002), pp. 1581-1587.
International Search Report and Written Opinion dated Sep. 11, 2008 cited in PCT/US2008/52623.
Chugh, Abhishek et al., "Towards Adaptive Caching for Parallel and Discrete Event Simulation," Proceedings of the 2004 Winter Simulation Conference, Washington, D.C. Dec. 5-8, 2004, Piscataway, NJ USA, IEEE, vol. 1,5 Dec. 2004, pp. 328-336, XP010754756, ISBN: 978-0-7803-8787-4.
Santos, Eunice et al., "Cache Diversity in Genetic Algorithm Design,"Flairs-00 Proceedings, May 22, 2000, pp. 107-111, XP002674909, Retrieved from the Internet: URL:http://www.aaai.org/Papers/FLAIRS/2000/FLAIRS00-021.pdf [retrieved on Apr. 26, 2012].
Walsh, Kevin et al., "Staged Simulation for Improving Scale and Performance of Wireless Network Simulations," International Conference on Machine Learning and Cybernetics, Proceedings of the 2003 Winter Simulation Conference, IEEE, Piscataway, NJ, USA, vol. CONF 36, Jan. 1, 2003, pp. 667-675, vol. 1, XP031099203, DOI: 10.1109/WSC.2003.1261482, ISBN: 978-0-7803-8131-5.
Young, Theodore et al., "Emergency Assessment with Sensors and Buildings: Advances in CT-Analyst Technology," Proceedings of the Chem-Bio Information Systems Conference 2004, Williamsburg, VA, Oct. 19-21, 2004, XP002674908, Retrieved from the Internet: URL:http://www.lcp.nrl.navy.mil/ct-analyst/Technical_Documents_files/Williamsburg_04.pdf [retrieved on Apr. 27, 2012].
Xu, Yong et al., "A GA Approach to the Optimal Placement of Sensors in Wireless Sensor Networks with Obstacles and Preferences," Consumer Communications and Networking Conference, 2006, 20 06 3rd IEEE Las Vegas, NV, USA Jan. 8-10, 2006, Piscataway, NJ, USA, IEEE, vol. 1, Jan. 8, 2006, pp. 127-131, XP010893144, DOI: 10.1109/CCNC.2006.1593001, ISBN: 978-1-4244-0085-0.
Extended European Search Report in counterpart EP Application No. 08780395.3, mailed May 10, 2012.
Michael J. Smith et al., "Sensor Location and Optimization Tool Set (SLOTS)," Internet, 2005, [JPO search date: Dec. 15, 2012]; URL http://www.dtic.mil/ndia/2005st_cbis/wednesday/smith2.pdf (also please see http://www.dtic.mil/ndia/2005st_cbis/wednesday/smith.pdf (Note: due to limitation of law or contract, there is a case in which part or all non-patent documents is not sent.).
Japanese Official Action in counterpart JP Application No. 2009-553661, mailed Dec. 20, 2012.
J. Boris et al., "Using CT-ANALYST to Optimize Sensor Placement," Proc. SPIE 5416, Chemical and Biological Sensing V, 14 (Aug. 13, 2004); doi:10.1117/12.542892.
Japanese Official Action in counterpart JP Application No. 2009-553661, mailed May 13, 2013.

* cited by examiner

SIMULATION CACHE TO EXPEDITE COMPLEX MODELING AND SIMULATION PROCESSES

STATEMENT REGARDING FEDERALLY SPONSORED RESEARCH OR DEVELOPMENT

This invention was made under U.S. Government Contract No. HDTRA1-05-C-0024. The U.S. Government may have certain rights in the invention.

FIELD OF THE INVENTION

The present invention relates to reducing the run time required for computer simulations.

BACKGROUND OF THE INVENTION

With the proliferation of chemical, biological, radiological and nuclear weapons, it is critical to be able to rapidly deploy equipment in the field to detect the release of these weapons for protection of military and civilian personnel.

Analysts require decision support tools that can assist them in planning for protection from these threats. These tools need to support sensor optimization in terms of their placement and sensor type mix (point and standoff sensors). To this end, efforts are being made to provide computer simulations and models of movement of a hazard over a three dimensional terrain based on the type of threat, weather and terrain conditions. Sensor location one of the more important factors in determining the efficacy of a particular sensor network in providing sufficient warning time and/or area coverage. There are numerous techniques to determine sensor location. One approach is to use advanced hazard environment modeling techniques coupled with sensor performance modeling routines and optimization algorithms. Hazard modeling techniques predict movement of a hazard based on the particular agent, weather and terrain in order to determine the nature, spatial extent and duration of the hazard. Sensor modeling techniques produce data representing a sensor's performance (will it detect or not) based on its ability to respond to the threat at various concentration thresholds. The optimization routine used to select the sensor location may include exhaustive searches and probabilistic models that allow determination of the optimal sensor layout given a range of threats and other criteria.

Computer modeling and simulation approaches heretofore known are too slow in producing results for sensor layouts. Traditional approaches require significant computational time and resources in order to generate data representing a four dimensional hazard environment. For each proposed or candidate location of a sensor or sensors, of which there may be hundreds or more, the conventional approach involves recalculating the hazard environment in order to determine whether and how fast a sensor layout will detect the hazard. For example, for a hazard scenario of 5 threats and 10 sensors, 50 hazard simulations or runs would be needed taking tens of hours of computing resources. There may be a much larger number of possible threats and sensor layouts to the point that the time required to determine an optimum sensor layout would not be able meet certain real-world scenarios.

Consequently, a method is needed to more rapidly determine optimum sensor locations in a hazard environment.

SUMMARY OF THE INVENTION

Briefly, a method is provided for determining optimum positions in a region for a plurality of sensors that are capable of detecting occurrence of a hazard in the region. The hazard may be a chemical, biological, and/or radiological hazard in solid, liquid or gas form. The method comprises simulating occurrence and movement over time of the hazard in the region and producing data representing movement of the hazard in the region. Next, a simulation is run whereby data representing movement of the hazard in the region is interacted with the data representing the sensors at each of a plurality of candidate locations in the region and for each of a plurality of sensor types. This computationally laborious task is performed one time. A "simulation cache" is provided that stores data representing interaction of the hazard with the sensors at each of the plurality of candidate locations in the region for each of the plurality of sensor types. Then, data is retrieved from the simulation cache as needed for evaluation a particular candidate sensor solution comprising one or more sensors of one or more sensor types at corresponding ones of the candidate locations. An optimization algorithm may be used to select a candidate sensor solution. The data that is retrieved from the simulation cache for a selected candidate sensor solution is evaluated with respect to certain performance criteria. Additional candidate solutions are selected, the corresponding data retrieved from the simulation cache, and the retrieved data evaluated. This selection and evaluation functions repeat until an exit criterion is met, such as convergence of selection, or maximum runtime expiration.

The simulation cache greatly reduces the time required to generate an optimum sensor layout because it separates the hazard modeling and sensor performance modeling from the optimization algorithm. Therefore, the more complex and computationally intensive hazard modeling is performed once and the key results are stored for access by the optimization algorithm. By capturing this data at one time for storage in the simulation cache, it is not necessary to re-run the hazard simulations for each candidate sensor location generated by the optimization algorithm.

DETAILED DESCRIPTION

Figure 1:
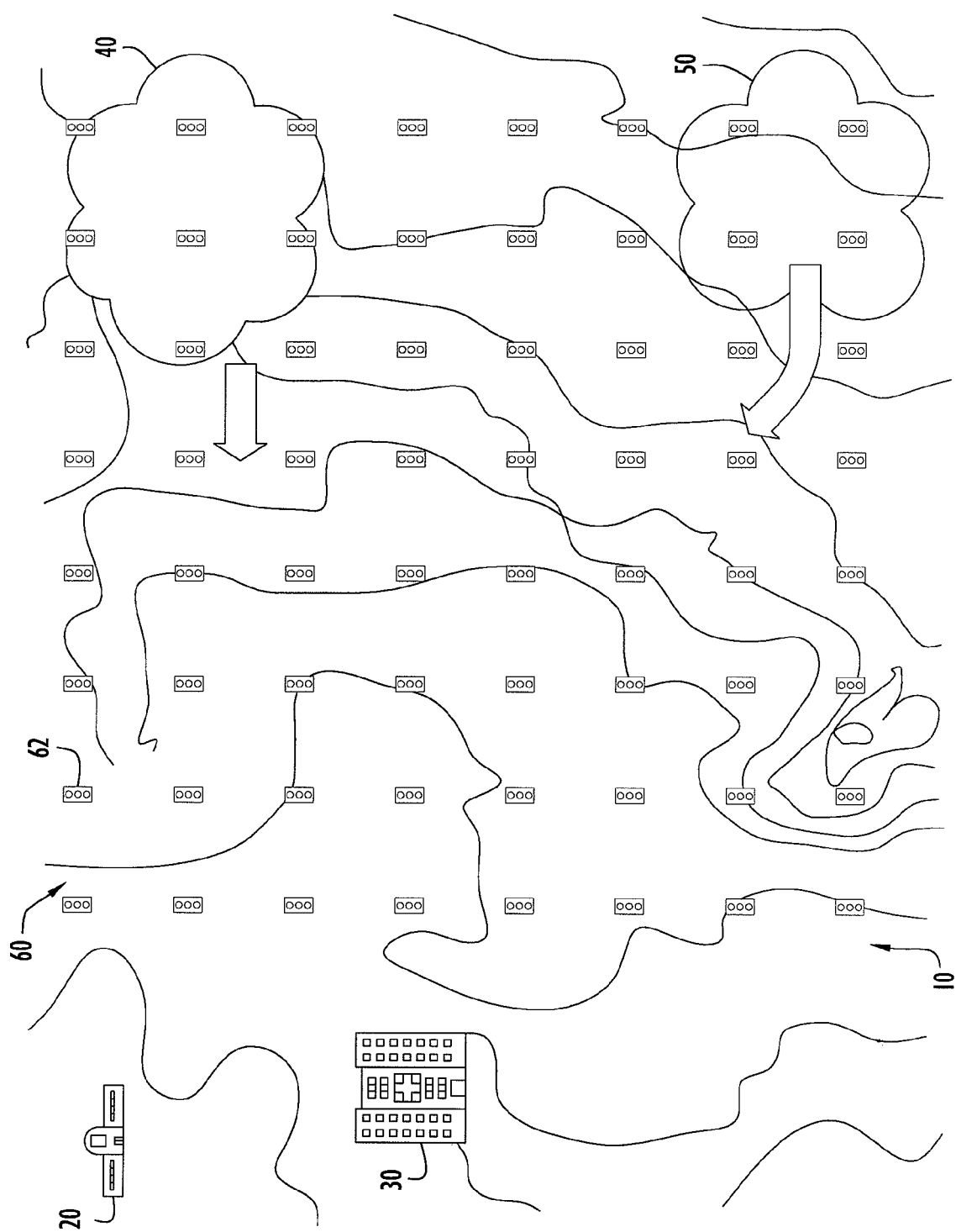
FIG. 1 is a diagram depicting a hazard-affected region in which it is desired to determine optimum locations for hazard detection sensors.

FIG. 1 illustrates a representative environment to which the present invention pertains. Specifically, a generalized map of a geographic region 10 is shown comprising landmarks such as a train station 20 and a hospital 30. One or more hazards shown at 40 and 50 may occur in the region 10 and it is desirable to determine where to position sensors in the region in order to detect occurrence of the hazard in order to minimize harm to people in the region and for other reasons. The hazards 40 and 50 may be the release in (liquid, solid or gas form) of a chemical, biological, and/or radiological substance or other agent harmful to humans or animals. The region 10 has a known terrain and generally known or predictable weather patterns. Also shown in FIG. 1 is a grid 60 comprised of a plurality of candidate positions 62 for sensors in a sensor array that can be deployed in the region. Given the terrain and normal weather patterns, it is desirable to determine optimal locations to place a set of N sensors (in an N sensor array) so that they will most effectively sense potential upwind hazards. In the exemplary environment shown in FIG. 1, it may be desirable to determine where to position the sensors in order to provide the hospital 30 and train station 20 the earliest possible warning of a hazard.

Figure 2:
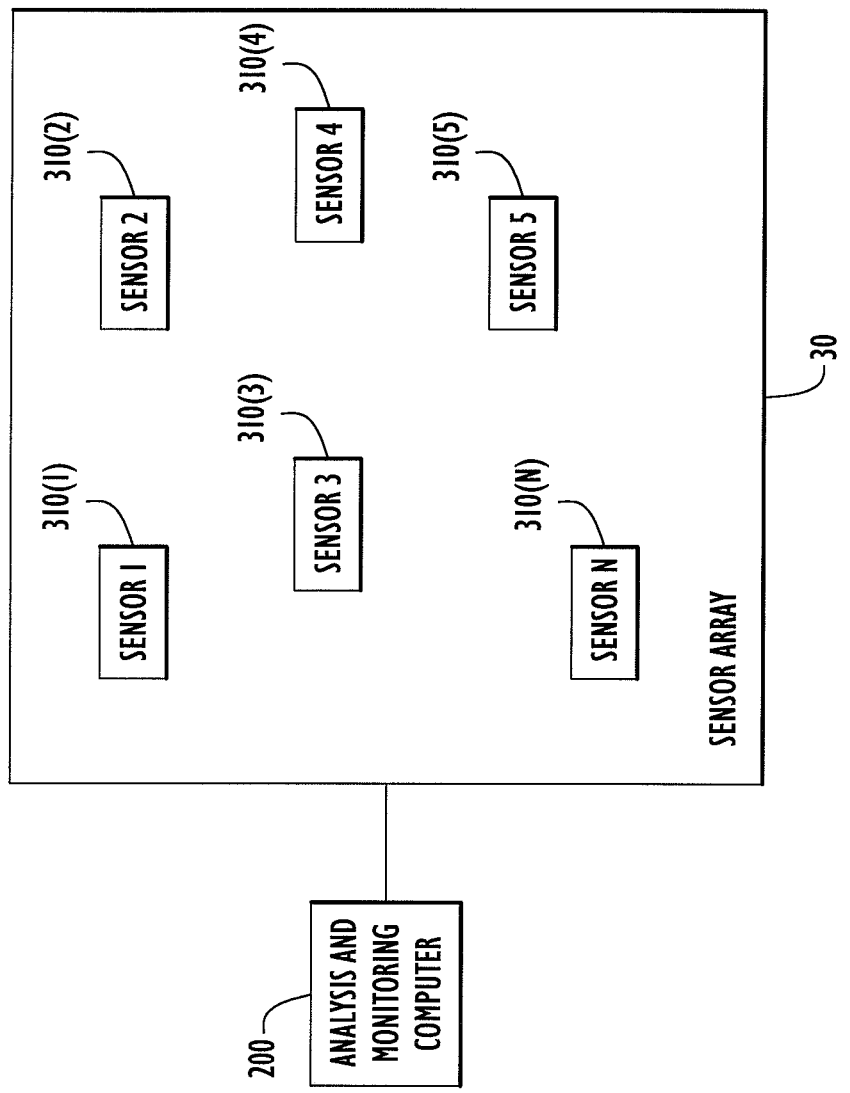
FIG. 2 is a block diagram of a hazard detection system comprising an array of hazard detection sensors and a computing apparatus that analyzes data from the sensors.

Turning to FIG. 2, a monitoring system 100 is shown comprising an analysis and monitoring computer 200 and a sensor array 300. The sensor array 300 comprises a plurality of sensors 310(1) to 310(N) of the same or different types. The sensors 310(1) to 310(N) are positioned at certain ones of the positions 62 shown in FIG. 1 that are determined to achieve a desired detection and warning capability in the region 10. Examples of sensor types are point sensors and stand-off sensors. Point sensors detect chemical/biological concentrations from surrounding air. Stand-off sensors use spectral returns from a laser to detect and identify a substance on a surface. Sensors also can vary by sensitivity to specific agents, false alarm rate, time to alarm or identify, physical size and other requirements, and importantly cost . . . . Another variation in sensor type is one that has a varying sensitivity to specific agents. Heterogeneous sensor types may be particular useful because it is possible that there may be a very limited number of a particular highly sensitive sensor type are available, whereas sensor types of a lesser sensitivity may be less costly and thus more readily available.

One method to determine the near-optimal position for the sensors 310(1) to 310(N) is to simulate a number of hazard clouds in 4-dimensional space (x, y, z, time), and then simulate sensors interacting with these hazards at various locations. The results of the performance of the interaction between the hazards and sensors are then combined using one of several possible algorithms, termed fitness functions, to produce a single rating value. The solution with the best performance, as defined by the fitness function, is chosen as the near-optimal solution. This is known as a combinatory optimization.

These simulations are relatively high cost calculations, meaning that they take a significant amount of time (months to years if re-running those simulations for each possible solution) to solve using conventional techniques. As the number of variables ((number of simulations, number of sensors, different types of sensors, etc.) in the environment increases, the number of possible combinations increases geometrically.

Figure 3:
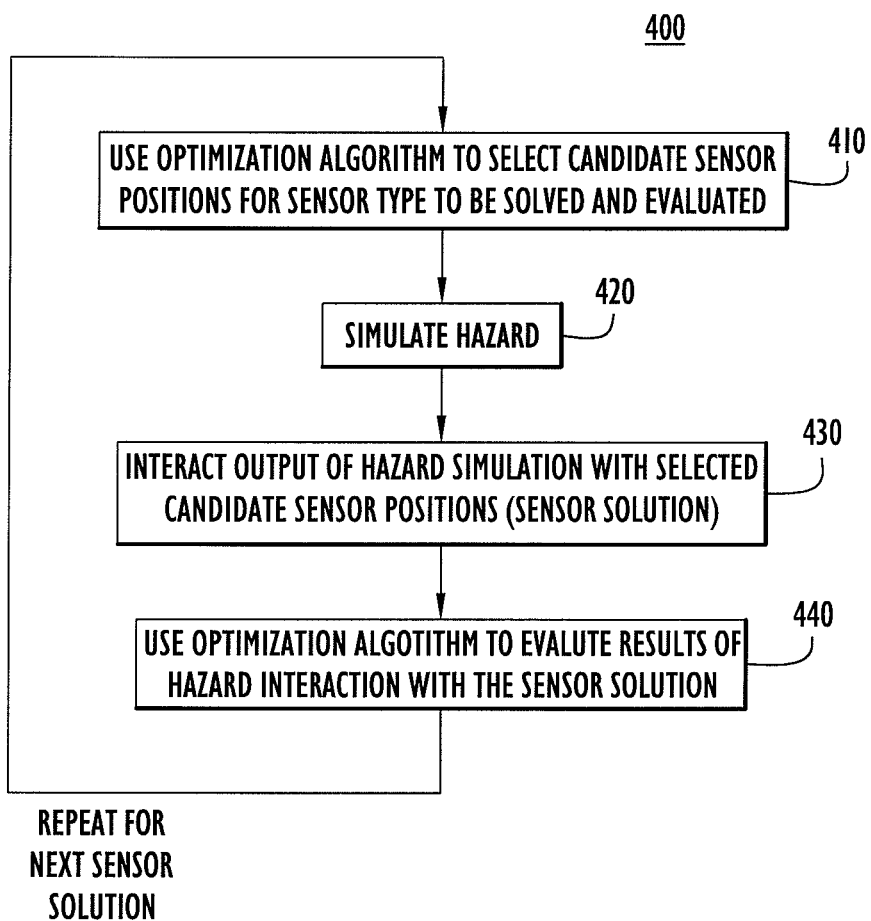
FIG. 3 is a flow chart of a conventional process flow for selecting optimum locations for sensors in a modeled hazard-affected region.

FIG. 3 illustrates a conventional process for determining the optimum position of the sensors in a sensor array. First, at 410, an optimization algorithm is used to select candidate sensor positions (locations in three dimensions) for a particular type of sensor. The candidate sensor positions may consist of candidate positions for each of a plurality of sensors in a sensor array that feeds inputs to an analysis computer such as shown in FIG. 2. The selected candidate sensor positions are referred to collectively as a "sensor solution" because they represent one possible solution of the process. Next, at 420, a hazard is simulated using any one of a several known (or hereinafter developed) hazard simulating techniques. The hazard simulation involves a computer model that simulates occurrence and movement over time of the hazard in a particular region based on the type of hazard, weather and terrain of the region. At 430, the output of the hazard simulation is interacted with data representing the selected candidate sensor positions and sensor type. The input to the interaction computation at 430 is the output of the hazard simulation and a set of coordinates representing the {x, y, z} location of each of the sensors and a type of sensor. Next, at 440, the optimization algorithm used at 410 evaluates the results of the interaction of the hazard with that sensor solution and provides a score or numerical indication of how successful the sensor solution would be based on the certain criteria set for the simulation. The process is repeated for the next sensor solution (candidate sensor locations) so that an evaluation or score is chosen for each sensor solution. The goal is then to choose the sensor solution that achieves the best score and the sensors can then be deployed based on the candidate locations of the sensor solution with the best score.

In terms of computational cost (time and complexity), selecting a sensor solution at 410 and evaluating the results at 440 is relatively small, but simulating the hazard at 420 and interacting the output of the hazard simulation with a sensor solution can be as much as 500 times more costly than the computations at 410 and 440. Worse still, the number of sensor solutions that may require evaluating can be extremely larger, such as 40,000 to 160,000 or more depending on the number of sensors used in the simulation and the number of types of different sensors.

Figure 4:
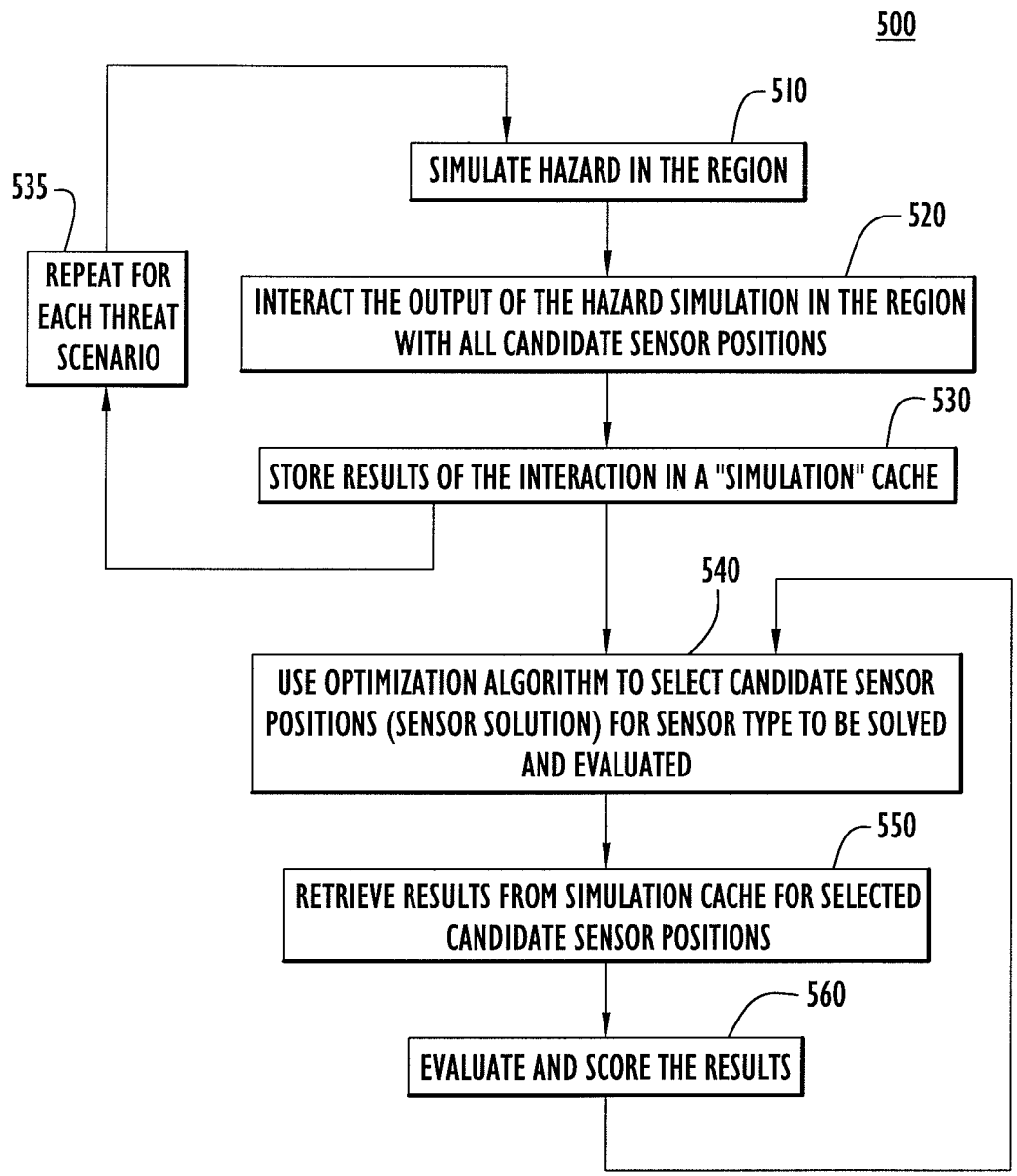
FIG. 4 is a flow chart of a process flow for selecting optimum sensor locations according to an embodiment of the present invention.

Turning to FIG. 4, the process 500 for determining the location of the sensors according to an embodiment of the present invention is now described. At 510, the occurrence and movement over time of the hazard in the region is simulated similar to 420 in FIG. 3. Data is produced at 510 that represents occurrence and movement of the hazard in the region. At 520, a simulation is executed to interact data representing occurrence and movement of the hazard in the region with data representing the sensors at each of a plurality of candidate locations in the region and for each of a plurality of sensor types so that all possible sensor location and type interaction results are accounted for. The candidate locations may be defined, for example, on a rectangular grid as shown in FIG. 1, though this is not required for purposes of the present invention, so long as the candidate sensor locations are limited in some manner.

Data representing interaction of the hazard with the sensors at each of the plurality of candidate locations in the region for each of the plurality of sensor types are stored at 530 in what is called a "simulation" cache. The data stored in the simulation cache may comprise alarm time (if an alarm is triggered on the sensor) indicating when after release of the hazard the sensor detects the hazard and the associated hazard concentration, at each candidate sensor position for each sensor type.

As shown at 535, the functions of 510 through 530 are repeated for a statistically significant set of threat scenarios, thus building a library of threat/sensor simulation interactions in the cache.

At 540, a loop is initiated in which an optimization algorithm is used to select one of the plurality of candidate sensor solutions to be evaluated, wherein each candidate solution comprises one or more sensors of one or more sensor types at corresponding ones of the candidate locations. Next, at 550, data for the selected candidate sensor solution are retrieved from the stored simulation cache. Then at 560, the retrieved data for the selected candidate sensor solution are evaluated and scored by the optimization algorithm. The loop comprising functions 540, 550 and 560 is executed again for the next candidate sensor solution to be evaluated. The next candidate sensor solution selected by the optimization algorithm at 540 may be based on knowledge gained by the evaluations made for previously selected candidate sensor solutions so that the optimization algorithm narrows or focuses its selection towards those solutions that have a chance of improving achievement of the desired outcome.

The optimization algorithm invoked at 540 may select a candidate solution that comprises a plurality of sensors of the same or different sensor type each at a corresponding one of the plurality of candidate locations. At 560, the optimization algorithm may be designed to find the candidate solution that optimizes a measure of performance subject to predetermined constraints. The measure of performance may be the time duration from the detection of a hazard to the time the hazard actually interacts with the protected or other locations of concern; and the predetermined constraints may be to provide sufficient advance warning of the hazard at one or more positions in or near the region. In other words, the time of alarm to time of contamination of an asset is vitally important and used as a normalized performance measure. For example, the evaluation function at 560 may involve scoring the selected candidate solution so as to find the solution that provides the earliest warning of the hazard to one or more assets or landmarks in or near the region, e.g., the hospital or train station shown in FIG. 1. Thus, the ultimate goal of the process 500 is to select the optimum one of the candidate sensor solutions by iterating the selection (540), retrieval (550) and evaluation functions (560).

The simulation of the interaction of the hazard with the sensors is run with the sensors at all of the candidate locations for each of a plurality of sensors types to be evaluated. By capturing this data at one time for storage in the simulation cache, it is not necessary to re-run the hazard simulations for each candidate sensor location generated by the optimization algorithm. It also is not necessary to re-run already cached information if additional threat scenarios are added to the problem space. The loop of 510 through 530 loop will need to be run only for the new scenarios.

The computation cost of the process 500 is much improved over the conventional process 400 shown in FIG. 3. Functions 540, 550 and 560 are the only functions that are repeated for each sensor solution to be evaluated and each of these functions have a very small computation cost (milliseconds). The function 510 of simulating the hazard has the same computation cost as the function 420 in the conventional process 400 shown in FIG. 3. The function 520 of interacting the hazard simulation output with all of the candidate sensor positions and sensor types has a rather large computation cost. However, it is performed only once per threat scenario, whereas in the conventional process 400 data from the hazard simulation is interacted the candidate sensor positions for each sensor solution (each time through the loop shown in FIG. 4). The function 530 of storing the results of the interaction in 520 to a simulation cache is performed only once per threat scenario and requires only a slightly higher computational cost than the functions 540, 550 and 560. Thus, in the process 500 of the present, the function with the highest computational cost is removed from the optimization loop and is performed only one time. Furthermore, the optimization loop in the process 500 is comprised of functions with very low computational cost. Thus, the process 500 is much faster than the conventional process 400.

Caching the simulation results allows the optimization algorithm to be run again for changes that do not change the hazards, thus removing the need to run the hazard simulation again. For example, the operational value of warning time thresholds could change. The addition or modification of placement constraints and even the addition or movement of critical assets and their relative importance can change.

Figure 5:
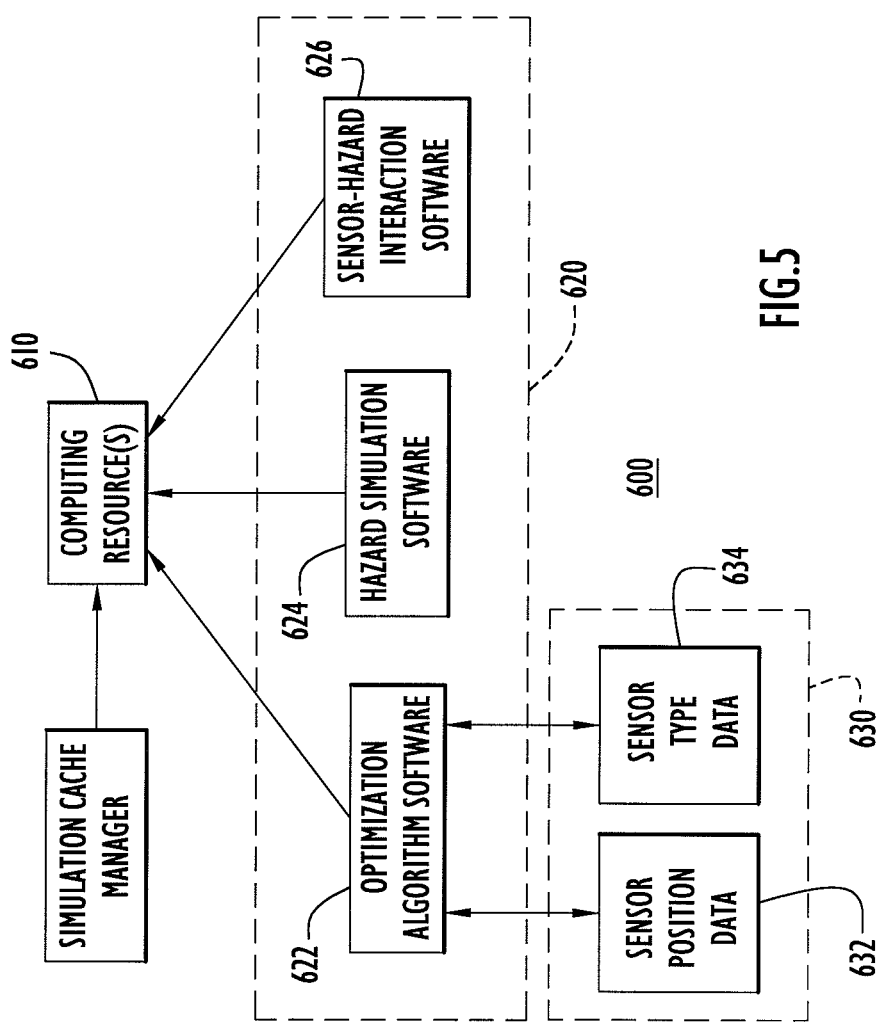
FIG. 5 is a block diagram of a computing system that employs the process flow shown in FIG. 4 according to an embodiment of the invention.

FIG. 5 illustrates a computing system 600 that may be used to perform the process 500 shown in FIG. 4. The system 600 comprises a computing resource(s) 610 consisting of one or more computers or server computers. The computing resource 610 is connected to memory 620 that stores optimization algorithm software 622, hazard simulation software 624 and sensor-hazard interaction software 626. There is also stored data in a database 630 for sensor position data 632 for all of the candidate sensor positions (sensor solutions) and sensor type data 634 for all of the types of sensors to be evaluated in the process 500. The optimization algorithm software 622 performs the optimization algorithm used in the process 500, the hazard simulation software 624 performs the hazard simulation in the process 500 and the sensor-hazard interaction software 626 performs the computations that interacts the hazard with the sensor position data for a sensor solution. Thus, the present invention may be embodied by instructions encoded on a computer readable medium that, when executed by a computer, perform the functions of process 500 shown in FIG. 4 and described herein.

The present invention is not limited to any particular simulation technology or optimization algorithm. For example, the hazard simulation algorithm may a transport and dispersion simulation, such as, for example, the Areal Location Of Hazardous Atmospheres (ALOHA) model or the Urban Hazard Prediction Assessment Capability (HPAC) model. With modifications to their driving software, these models can be used to store, on a fixed interval (e.g., 3 seconds) the location of the hazard in 3 dimensions. The optimization algorithm may employ a heuristic technique such as a genetic algorithm, or may use complete enumeration (i.e., exhaustive search) or gradient descent techniques. A genetic algorithm searches for solutions using the biological evolution principle of natural selection (survival of the fittest, crossbreeding and mutation). The term "genetic" is used to describe this type of algorithm because the solutions are represented as strings of values analogous to chromosomes and genes. A genetic algorithm starts with a set of initial solutions (typically via random solution generation) and produces increasingly better solutions by selectively combining (called crossover) and stochastically altering (called mutation) existing solutions and weeding out poor ones to converge on a near optimal solution as determined by a specified performance criterion (referred to as the fitness function). This amounts to searching a large multidimensional (and possibly discontinuous) search space to find the solution with the best fitness function value.

The optimization algorithm used in the process 500 may be configured to randomly select candidate sensor locations, and then use further analysis to explore potential solutions. If a genetic algorithm is used, crossover and mutation techniques may be used to further explore the solution space. The likelihood that any solution is kept or used as a basis for evolution of future solutions depends on a score given to a sensor solution.

The techniques described herein according to embodiments of the present invention provide an efficient method for capturing model and simulation results for processing by various optimization algorithms. The techniques are useful even when the hazard simulation output varies with identical input and thus provides slightly different solutions each run, because the sensor interaction simulations do not vary with input, and thus caching still maintains integrity of the process.

Nevertheless, the simulation cache technique described herein may apply to any simulation process where candidate solution combinations can be enumerated and the simulation results are repeatable. For example, and not by way of limitations, it may be used to store integrated dose data for purposes of calculating individual exposure of personnel at varying degrees of protection from a hazard. Instead of using the simulation that interacts notional sensors with instantaneous point concentrations of detectable agent, a replacement simulation would track the integrated dosage for exposed persons with N classes of protection, and report the time at which each of those location/protection class combinations would exhibit various symptoms such as meiosis, impairment, unconsciousness and death. These times and symptom categories would be cached in the same manner as the detection times in process 500. Other decisions such as troop placement and multiple protection profiles could be optimized, though likely with a much different fitness function than the sensor location optimization.

To summarize some advantages of the present invention, the use of a simulation cache as described herein greatly reduces the time required to generate an optimum sensor layout. The simulation cache allows for separating the hazard modeling and sensor performance modeling from the optimization algorithm. Therefore, the more complex and computationally intensive hazard modeling is performed a single time and the key results are stored for access by the optimization algorithm. Sensor locations are limited to a plurality of candidate positions or locations. The simulation of the interaction of the hazard with the sensors is run with the sensors at all of the candidate locations. The simulation cache then stores the data resulting from the interaction (alarm time if an alarm is triggered on the sensor and associated hazard concentration at the sensor) for each sensor at its candidate location, for each hazard simulation and for each sensor type. By capturing this data at one time for storage in the simulation cache, it is not necessary to re-run the hazard simulations for each candidate sensor location generated by the optimization algorithm. As a result, there is a substantial reduction in the run time. Furthermore, it becomes possible to perform ad hoc optimization analysis without involving or accessing the hazard and sensor models. This means that less computational resources are needed for running the optimization algorithm when it is necessary to add or subtract sensors and other constraints typical of real-world scenarios.

The system and methods described herein may be embodied in other specific forms without departing from the spirit or essential characteristics thereof. The foregoing embodiments are therefore to be considered in all respects illustrative and not meant to be limiting.

What is claimed is:

1. A method for determining optimum positions in a region for a plurality of sensors, wherein the sensors are capable of detecting occurrence of a hazard in the region, comprising:
   a. simulating occurrence and movement over time of the hazard in the region to produce data representative thereof;
   b. simulating a reaction of sensors at a set of all possible candidate sensor locations in the region and for each of a plurality of sensor types responsive to the simulated occurrence and movement of the hazard over time;
   c. storing in a simulation cache data resulting from the simulated reaction of the sensors at the set of all possible candidate sensor locations in the region for each of the plurality of sensor types responsive to the simulated occurrence and movement of the hazard over time;
   d. selecting one of a plurality of candidate sensor solutions, wherein each candidate sensor solution comprises one or more sensors of one or more sensor types at corresponding selected ones of the candidate sensor locations within the set of all possible candidate sensor locations;
   e. retrieving from the simulation cache data for the selected candidate sensor solution from the stored data;
   f. evaluating the data retrieved from the simulation cache from said (e) retrieving with respect to performance criteria for the selected one of the candidate sensor solutions; and
   g. selecting another one of the plurality of candidate sensor solutions and repeating (e) and (f), the another one of the plurality of candidate sensor solutions differing from the one of the plurality of candidate sensor solutions in at least one candidate sensor location or at least one sensor type.

2. The method of claim 1, and further comprising selecting one of the candidate sensor solutions based on said (f) evaluating.

3. The method of claim 1, wherein (d) selecting comprises selecting one of the plurality of candidate sensor solutions using an optimization algorithm that finds the sensor location(s) to optimize said performance criteria.

4. The method of claim 3, wherein (d) selecting comprises executing a genetic algorithm that searches for a candidate sensor solution among the plurality of candidate sensor solutions using biological evolution principles.

5. The method of claim 1, wherein (f) evaluating comprises assigning a score to the candidate sensor solution, and wherein (g) selecting comprises selecting another candidate sensor solution based on scores from (f) evaluating a plurality of other candidate sensor solutions.

6. The method of claim 1, wherein (f) evaluating comprises scoring data comprises for the selected candidate solution so that after a plurality of iterations of said (e) and (f) for a plurality of candidate sensor solutions, said (d) selecting finds the candidate sensor solution that provides an earliest average warning of the hazard to one or more assets or landmarks in or near the region.

7. The method of claim 1, wherein (d) selecting comprises selecting a candidate sensor solution that comprises a plurality of sensors of the same or different sensor type each at a corresponding one of the plurality of candidate sensor locations.

8. The method of claim 1, wherein said (a) simulating occurrence and movement over time, said (b) simulating reaction, and said (c) storing data resulting from the simulated reaction is performed for each of a plurality of hazards.

9. The method of claim 1, further comprising:
   selecting another one of the plurality of candidate sensor solutions and repeating said (e) retrieving;
   evaluating the data retrieved from the simulation cache with respect to performance criteria for the selected another one of the plurality of candidate sensor solutions;
   assigning a corresponding evaluation score to the selected another one of the plurality of candidate sensor solutions based on the evaluating the data retrieved from the simulation cache with respect to the performance criteria for the selected one of the candidate sensor solutions; and
   selecting an optimal one of the candidate sensor solutions based on the evaluation score assigned to the selected one of the plurality of candidate sensor solutions and the selected another one of the plurality of candidate sensor solutions.

10. The method of claim 9, wherein selecting another one of the candidate sensor solutions comprises the another one of the candidate sensor solutions based on the evaluation score assigned to the selected one of the candidate sensor solutions in said (g) assigning.

11. A method for determining optimum positions in a region for a plurality of sensors, wherein the sensors are capable of detecting occurrence of a hazard in the region, comprising:
  a. simulating occurrence and movement over time of the hazard in the region to produce data representative thereof;
  b. simulating a reaction of sensors at a set of all possible candidate sensor locations in the region and for each of a plurality of sensor types responsive to the simulated occurrence and movement of the hazard over time;
  c. storing in a simulation cache alarm data resulting from the simulated reaction of the sensors at the set of all possible candidate sensor locations in the region for each of the plurality of sensor types responsive to the simulated occurrence and movement of the hazard over time, said alarm data indicating whether and when an alarm condition occurs at each of the plurality of candidate sensor locations for each of the plurality of sensor types;
  d. selecting one of a plurality of candidate sensor solutions using an optimization algorithm, wherein each candidate sensor solution comprises one or more sensors of one or more sensor types at corresponding selected ones of the candidate sensor locations within the set of all possible candidate sensor locations;
  e. retrieving from the simulation cache data for the selected candidate sensor solution from the stored data; and
  f. evaluating and scoring the retrieved data from said (e) retrieving with respect to performance criteria for the selected one of the candidate sensor solutions.

12. The method of claim 11, and further comprising:
repeating said (d) selecting to select another one of the plurality of candidate sensors solutions based on said (f) evaluating so as to ultimately find an a candidate sensor solution that optimizes said performance criteria.

13. The method of claim 11, wherein (d) selecting comprises using an optimization algorithm that searches for a candidate sensor solution among the plurality of candidate sensor solutions using biological evolution principles.

14. The method of claim 11, wherein said (d) selecting comprises selecting the one of the plurality of candidate sensor solutions that comprises a plurality of sensors of the same or different sensor type each at a corresponding one of the plurality of candidate sensor locations.

15. The method of claim 11, further comprising selecting an optimal candidate sensor solution that provides an earliest warning of the hazard to one or more assets or landmarks in or near the region based on the assigned score assigned to each of the plurality of candidate sensor solutions after a plurality of iterations of said (g) evaluating and (h) assigning for each of the plurality of candidate sensor solutions.

16. A non-transitory computer readable medium encoded with instructions that, when executed by a computer, cause the computer to generate output useful in determining optimum positions in a region for a plurality of sensors, wherein the sensors are capable of detecting occurrence of a hazard in the region, comprising:
  a. simulating occurrence and movement over time of the hazard in the region to produce data representative thereof;
  b. simulating a reaction of sensors at a set of all possible candidate sensor locations in the region and fore ach of a plurality of sensor types responsive to the simulated occurrence and movement over time;
  c. storing in a simulation cache data resulting from the simulated reaction of the sensors at the set of all possible candidate sensor locations in the region for each of the plurality of sensor types responsive to the simulated occurrence and movement of the hazard over time with the data representing the sensors at the set of all possible candidate sensor locations in the region for each of the plurality of sensor types;
  d. selecting one of a plurality of candidate sensor solutions, wherein each candidate sensor solution comprises one or more sensors of one or more sensor types at corresponding selected ones of the candidate sensor locations within the set of all possible candidate sensor locations;
  e. retrieving from the simulation cache data for the selected candidate sensor solution from the stored data;
  f. evaluating the data retrieved from the simulation cache from said (e) retrieving with respect to performance criteria for the selected one of the candidate sensor solutions; and
  g. selecting another one of the plurality of candidate sensor solutions and repeating (e) and (f), the another one of the plurality of candidate sensor solutions differing from the one of the plurality of candidate sensor solutions in at least one candidate sensor location or at least one sensor type.

17. The computer readable medium of claim 16, wherein said instructions for (c) storing data identified with the hazard comprise instructions for storing alarm data indicating whether and when an alarm condition occurs at each of the plurality of candidate sensor locations for each of the plurality of sensor types.

18. The computer readable medium of claim 16, wherein said instructions for (d) selecting comprises instructions for executing a genetic algorithm that searches for a candidate sensor solution among the plurality of candidate sensor solutions using biological evolution principles.

19. The computer readable medium of claim 16, wherein said instructions for (d) selecting comprises instructions for selecting the one of the plurality of candidate sensor solutions that comprises a plurality of sensors of the same or different sensor type each at a corresponding one of the plurality of candidate sensor locations.

20. The computer readable medium of claim 16, further comprising instructions comprising selecting an optimal candidate sensor solution that provides an earliest warning of the hazard to one or more assets or landmarks in or near the region based on the assigned score assigned to each of the plurality of candidate sensor solutions after a plurality of iterations of said (f) evaluating and (g) assigning for each of the plurality of candidate sensor solutions.

* * * * *